United States Patent

McLaren et al.

[11] Patent Number: 5,493,024
[45] Date of Patent: Feb. 20, 1996

[54] 3,4,N-TRISUBSTITUTED-4,5-DIHYDRO-1H-PYRAZOLE-1-CARBOXAMIDES AND THEIR USE AS INSECTIOIDES

[75] Inventors: Kevin L. McLaren, Concord; Mark B. Hertlein, Pleasant Hill; James T. Pechacek, Clayton; Michael J. Ricks, Concord; Yulan C. Tong, Walnut Creek, all of Calif.

[73] Assignee: DowElanco, Indianapolis, Ind.

[21] Appl. No.: 71,870

[22] Filed: Jun. 2, 1993

Related U.S. Application Data

[63] Continuation of Ser. No. 684,525, Apr. 11, 1991, abandoned.

[51] Int. Cl.$^6$ .................. C07D 237/04; C07D 239/24; C07D 215/12; C07D 211/72
[52] U.S. Cl. .................. 544/259; 544/298; 544/315; 544/334; 544/335; 544/406; 544/408; 544/409; 546/290; 546/314; 546/340; 546/174
[58] Field of Search .................. 546/290, 314, 546/340, 174; 544/239, 298, 315, 334, 335, 406, 405, 409

[56] References Cited

U.S. PATENT DOCUMENTS

| | | | |
|---|---|---|---|
| 1,980,638 | 11/1934 | Scheuing et al. | 546/340 |
| 3,371,096 | 2/1968 | Brust et al. | 546/340 |
| 3,991,073 | 11/1976 | Mulder et al. | 548/369 |
| 4,010,271 | 3/1977 | Mulder et al. | 514/403 |
| 4,018,910 | 4/1977 | Winter et al. | 546/340 |
| 4,070,365 | 1/1978 | van Daalen et al. | 548/379 |
| 4,156,007 | 5/1979 | van Daalen et al. | 514/403 |
| 4,174,393 | 11/1979 | val Daalen et al. | 548/379 |
| 4,342,782 | 8/1982 | Cragoe, Jr. | 546/340 |
| 4,402,961 | 9/1983 | Dubroeucq et al. | 514/314 |
| 4,506,073 | 3/1985 | Balli et al. | 546/64 |
| 4,605,656 | 8/1986 | Dorn | 514/255 |
| 4,612,321 | 9/1986 | Terao et al. | 514/338 |
| 4,681,944 | 7/1987 | Ippolito et al. | 546/340 |
| 4,839,376 | 6/1989 | Yamashita et al. | 514/406 |
| 4,888,340 | 12/1989 | Neh et al. | 514/403 |
| 4,960,784 | 10/1990 | Lahm | 514/403 |
| 5,116,844 | 5/1992 | Dickinson | 514/269 |

FOREIGN PATENT DOCUMENTS 158103 12/1982 Germany .

OTHER PUBLICATIONS

Weber et al., *Zeitschrift fur Chemie*, 1972, 12(4), 132–133.
Chem Abstr. vol. 108, #112,429 (1988).

*Primary Examiner*—Mukund J. Shah
*Attorney, Agent, or Firm*—D. Wendell Osborne

[57] ABSTRACT

3,4,N-triaryl-4,5-dihydro-1H-pyrazole-1-carboxamide compounds having an aryl moiety in the 4-position that is an optionally substituted pyridinyl, pyrimidinyl, pyridazinyl, pyrazinyl, or quinolinyl moiety and aryl moieties in the 3-position and the N-position that are optionally substituted phenyl, pyridinyl, pyrimidinyl, pyridazinyl, pyrazinyl, or quinolinyl moieties, such as N-(4-chlorophenyl)-4,5-dihydro-3-(4-fluorophenyl)-4-(5-trifluoromethyl-2-pyridinyl)-1H-pyrazole-1-carboxamide, were prepared and found to possess insecticidal utility. 1,2-Diarylethanone compounds were converted to 1,2-diaryl-2-propen-1-one compounds by treatment with bis(dimethylamino)methane, the 1,2-diaryl-2-propen-1-one compounds were converted to 3,4-diaryl-4,5-dihydro-1H-pyrazole compounds by treatment with hydrazine, and the 3,4-diaryl-4,5-dihydro-1H-pyrazole compounds were converted to the insecticidal subject compounds by treatment with an aryl isocyanate.

16 Claims, No Drawings

3,4,N-TRISUBSTITUTED-4,5-DIHYDRO-1H-PYRAZOLE-1-CARBOXAMIDES AND THEIR USE AS INSECTIOIDES

This application is a continuation of U.S. Ser. No. 07/684,525, filed Apr. 11, 1991, abandoned.

BACKGROUND OF THE INVENTION

The present invention relates to 3,4,N-trisubstituted-4,5-dihydro-1H-pyrazole-1-carboxamide compounds wherein the substituent in the 4-position is an optionally substituted pyridinyl, quinolinyl, pyrimidinyl, pyrazinyl, or pyridazinyl moiety and the substituents in the 3-position and the N-position are optionally substituted phenyl, pyridinyl, quinolinyl, pyrimidinyl, pyrazinyl, or pyridazinyl moieties and to the insecticidal utility of these compounds.

The control of insects is critical to modern agriculture and to the maintenance of public health. Although many compounds that control insects are known, the discovery of new insecticides that are more effective, less toxic to man and the environment, less expensive to manufacture, or have other outstanding attributes are constantly sought and when found highly valued.

A number of 3,4,N-trisubstituted-4,5-dihydro-1H-pyrazole-1-carboxamide compounds wherein all of the substituents are optionally substituted phenyl moieties have been prepared and found to possess insecticidal activity (U.S. Pat. Nos. 4,888,340, 4,174,393, and 4,070,365). 3,5,N-Trisubstituted-4,5-dihydro-1H-pyrazole-1-carboxamide compounds possessing unsubstitued pyridinyl as well as phenyl substituent moieties in the 3- and 5-positions and their insecticidal utility have also been disclosed (U.S. Pat. No. 3,991,073).

SUMMARY OF THE INVENTION

It has now been found that novel 3,4,N-trisubstituted-4,5-dihydro-1H-pyrazole-1-carboxamide compounds wherein the substituent in the 4-position is an optionally substituted pyridinyl, quinolinyl, pyrimidinyl, pyrazinyl, or pyridazinyl moiety and the substituents in the 3-position and the N-position are optionally substituted phenyl, pyridinyl, quinolinyl, pyrimidinyl, pyrazinyl, or pyridazinyl moieties possess surprisingly good insecticidal utility.

In particular, 3,4,N-triaryl-4,5-dihydro-1H-pyrazole-1-carboxamide compounds of the formula

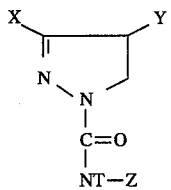

wherein

Y represents 2-, 3-, or 4-pyridinyl, 2- or 3-quinolinyl, 2-, 4-, or 5-pyrimidinyl, 2-pyrazinyl, or 3- or 4-pyridazinyl, each optionally substituted with 1 or 2 compatible substituents selected from F, Cl, Br, CN, COQ, R, OR', SR', SOR', $SO_2R'$, $NO_2$, and OAr;

X represents Y, phenyl, or phenyl substituted in the 4-position with F, Cl, Br, CN, COQ, R, OR', SR', SOR', $SO_2R'$, $NO_2$, or OAr and/or in the 3-position with F, Cl, Br, CN, R, or OR';

Z represents Y, phenyl, or phenyl substituted in the 4-position with F, Cl, Br, CN, COQ, R, OR', SR', SOR', $SO_2R'$, $OSO_2R'$, $NO_2$, or OAr and optionally in the 2-position with F and optionally in the 3- or 5-position with F, Cl, Br, CN, R, or OR';

T represents H, R'CO, or R"OCO;

R represents $C_1$–$C_3$ alkyl, $C_2$–$C_3$ alkenyl, or $C_2$–$C_3$ alkynyl optionally singly to completely substituted with fluorine or chlorine;

R' represents $C_1$–$C_3$ alkyl optionally singly to completely substituted with fluorine or chlorine;

R" represents $C_1$–$C_4$ alkyl, $C_3$–$C_4$ alkenyl, or $C_3$–$C_4$ alkynyl;

Ar represents phenyl optionally substituted with 1 or 2 compatible substituents selected from F, Cl, Br, CN, COQ, R, OR', SR', SOR', $SO_2R'$, and $NO_2$; and Q represents OR", SR", $NH_2$, NHR", or NR"$_2$.

Such compounds are novel, are useful for controlling insects when applied in an insecticidally effective amount to insects or the locus thereof, and are components of insecticidal compositions comprising an insecticidally effective amount in combination with an agriculturally acceptable carrier or adjuvant.

Dihydropyrazole compounds of the above formula wherein Y represents an optionally substituted pyridinyl, quinolinyl, pyrimidinyl, pyrazinyl, or pyridazinyl moiety and X and Z each represent optionally substituted phenyl moieties and the use of these compounds as insecticides are often preferred.

The invention includes certain intermediates involved in preparing the novel insecticidal compounds, including precursor 1,2-diarylethanones, 1,2-diaryl-2-propen-1-ones, and 3,4-diaryl-4,5-dihydropyrazoles.

DETAILED DESCRIPTION OF THE INVENTION

The compounds of the present invention are 3,4,N-triaryl-4,5-dihydro-1H-pyrazole-1-carboxamide compounds of the generic formula

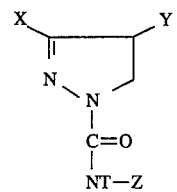

wherein

Y represents 2-, 3-, or 4-pyridinyl, 2- or 3-quinolinyl, 2-, 4-, or 5-pyrimidinyl, 2-pyrazinyl, or 3- or 4-pyridazinyl, each optionally substituted with 1 or 2 compatible substituents selected from F, Cl, Br, CN, COQ, R, OR', SR', SOR', $SO_2R'$, $NO_2$, and OAr;

X represents Y, phenyl, or phenyl substituted in the 4-position with F, Cl, Br, CN, COQ, R, OR', SR', SOR', $SO_2R'$, $NO_2$, or OAr and/or in the 3-position with F, Cl, Br, CN, R, or OR';

Z represents Y, phenyl, or phenyl substituted in the 4-position with F, Cl, Br, CN, COQ, R, OR', SR', SOR', $SO_2R'$, $OSO_2R'$, $NO_2$, or OAr and optionally in the 2-position with F and optionally in the 3- or 5-position with F, Cl, Br, CN, R, or OR';

T represents H, R'CO, or R"OCO;

R represents $C_1$–$C_3$ alkyl, $C_2$–$C_3$ alkenyl, or $C_2$–$C_3$ alkynyl optionally singly to completely substituted with fluorine or chlorine;

R' represents $C_1$–$C_3$ alkyl optionally singly to completely substituted with fluorine or chlorine;

R" represents $C_1$–$C_4$ alkyl, $C_3$–$C_4$ alkenyl, or $C_3$–$C_4$ alkynyl;

Ar represents phenyl optionally substituted with 1 or 2 compatible substituents selected from F, Cl, Br, CN, COQ, R, OR', SR', SOR', $SO_2R'$, and $NO_2$; and Q represents OR", SR", $NH_2$, NHR", or $NR"_2$.

Such compounds are 3,4,N-triaryl-4,5-dihydro-1H-pyrazole-1-carboxamide compounds wherein the aryl moiety in the 4-position is a six membered aromatic heterocycle having one or two nitrogen atoms or quinoline.

4,5-Dihydro-1H-pyrazole compounds are sometimes informally referred to as 2-pyrazoline or Δ2-pyrazoline compounds. Chemical Abstracts nomenclature has generally been used to name the compounds of this invention.

The term "compatible substituents" is used herein to define combinations of substituents that when present together in the designated positions do not interfere with each other so as to make the subject compound unmakable or unstable.

The compounds of Formula I exist in two enantiomeric isomer forms because the 4-position ring carbon atom is asymmetrically substituted. The present invention relates to each of the enantiomeric isomers and to all mixtures of these isomers. It is anticipated that the enantiomeric isomers will both have utility as insecticides but that one of the enantiomeric isomers will be generally more efficacious than the other.

Insecticidal dihydropyrazole compounds of the invention wherein Y represents a substituted 2-pyridinyl, 3-pyridinyl, 2-pyrimidinyl, 5-pyrimidinyl, 2-pyrazinyl, or 3-pyridazinyl moiety are often preferred. Such compounds wherein Y represents a 5-substituted-2-pyridinyl, 5-substituted-2-pyrimidinyl, 6-substituted-3-pyridazinyl, or 5-substituted-2-pyrazinyl moiety are generally more preferred in some circumstances and such compounds wherein Y represents a 6-substituted-3-pyridinyl or 2-substituted-5-pyrimidinyl moiety are generally more preferred in other circumstances. Compounds wherein Y represents a 5-substituted-2-pyridinyl or a 5-substituted-2-pyrimidinyl moiety are sometimes most preferred. Compounds of the invention wherein the substituents of the Y heterocycle are selected from F, Cl, Br, CN, $CF_3$, and $OCF_3$ are generally preferred.

Insecticidal dihydropyrazole compounds of the invention wherein X represents substituted phenyl (as defined hereinabove) or wherein Z represents substituted phenyl (as defined hereinabove) are often preferred. Compounds wherein both X and Z represent substituted phenyl are generally more preferred. Such compounds wherein X and Z each, independently represent substituted phenyl wherein the substituent is in the 4-position are generally highly preferred and those wherein that substituent is selected from F, Cl, Br, $CF_3$, $OCF_3$, $OCF_2CF_2H$, and $SCF_3$ are usually most preferred. Compounds wherein T represents H are preferred.

The specifically preferred compounds include 4,5-dihydro-3-(4-fluorophenyl)-N-(4-trifluoromethoxyphenyl)-4-(5-trifluoromethyl-2-pyridinyl)-1H-pyrazole-1-carboxamide, N-(4-chlorophenyl)-4,5-dihydro-3-(4-fluorophenyl)-4-(5-trifluoromethyl-2-pyridinyl)-1H-pyrazole-1-carboxamide, 4,5-dihydro-3-(4-fluorophenyl)-N-(4-trifluoromethylphenyl)-4-(5-trifluoromethyl-2-pyridinyl)-1H-pyrazole-1-carboxamide, 3-(4-chlorophenyl)-4-(5-cyano-2-pyridinyl)-4,5-dihydro-N-(4-trifluoromethoxyphenyl)-1H-pyrazole-1-carboxamide, and 4-(5-chloro-2-pyrimidinyl)-4,5-dihydro-3-(4-fluorophenyl)-N-(4-trifluoromethoxyphenyl)-1H-pyrazole-1-carboxamide.

The insecticidal compounds of the present invention can be prepared by the reaction of an appropriate 3,4-disubstituted 4,5-dihydro-1H-pyrazole compound of Formula I with an appropriate isocyanate compound of Formula II as illustrated below.

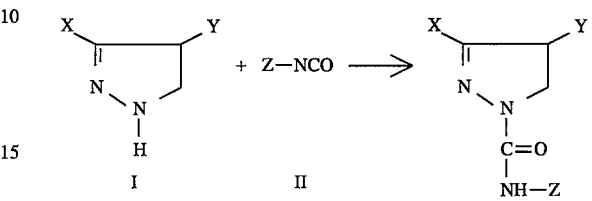

In Formulas I and II, X, Y, and Z are defined as hereinbefore for the insecticidal compounds of the invention. The reaction is generally effected by combining the 3,4-disubstituted 4,5-dihydro-1H-pyrazole and the isocyanate in the presence of an inert organic solvent, such as methylene chloride, 1,2-dichloroethane, chlorobenzene, toluene, acetonitrile, and the like, at a temperature of about 0° C. to about 60° C. and, typically, with agitation. The reaction takes place fairly rapidly, usually in about 0.1 to 20 hours. The 3,4,N-trisubstituted-4,5-dihydro-1H-pyrazole-1-carboxamide products are solids and can be recovered by conventional means, such as by filtration, centrifugation, or removal of the volatiles by evaporation. The initially recovered products can be further purified by conventional means, such as by recrystallization.

The insecticidal compounds of the invention wherein T represents R'CO or R"OCO can be prepared from the corresponding insecticidal compound wherein T represents H by treatment with a base, such as sodium hydride or potassium carbonate, and an appropriate acylating agent, such as acetyl chloride or trifluoroacetic anhydride, or an appropriate alkoxycarbonylating agent, such as ethyl chloroformate in a solvent, such as N,N-dimethylformamide or acetonitrile. The mixture is allowed to react at about ambient temperature and the product is recovered by conventional means.

The appropriate 3,4-disubstituted 4,5-dihydro-1H-pyrazole compounds of Formula I can be prepared by treatment of an appropriately substituted propenone compound of Formula III with hydrazine.

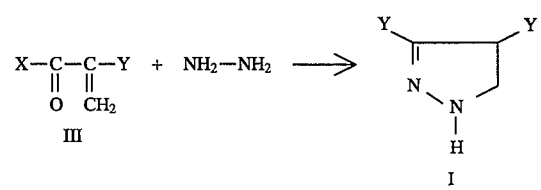

The reaction is typically effected by adding hydrazine, usually as the hydrate, to a solution of the propenone in a solvent, such as N,N-dimethylformamide or trifluoroacetic acid, at temperatures of about 0° C. to about 60° C. with agitation. After a reaction period of about 1 to about 8 hours the mixture is poured onto a mixture of ice and water with vigorous stirring. In those cases where the desired product precipitates as a solid, it can be recovered by filtration. In those cases where the desired product forms an oil, it can be recovered by extraction into an immiscible organic solvent, such as ether, and, if desired, further isolated by evaporation of the solvent. Compounds of Formula I are generally unstable and degrade on attempted recrystallization or distillation. Accordingly, the crude products obtained are generally not further purified before being employed as intermediates. The 3,4-disubstituted-4,5-dihydro-1H-pyrazole compounds of Formula I wherein X and Y are as defined above are novel compounds and are a further aspect of the invention.

The propenone compounds of Formula III can be prepared by the reaction of bisdimethylaminomethane and acetic anhydride with the appropriately substituted ethanone compound of Formula IV.

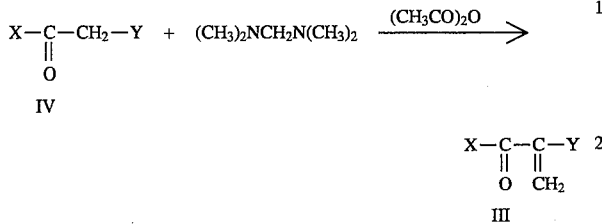

The reaction is generally carried out by adding excess acetic anhydride to a mixture of the ethanone compound of Formula IV in excess bisdimethylaminomethane at about 0° C. with agitation. The desired propenone compound of Formula III can be recovered by conventional means, such as by adding water and ether, separating the phases, and evaporating the volatile materials from the ethereal phase. The propenone compounds of Formula III wherein X and Y are defined as above are novel compounds and are a further aspect of the invention.

Certain of the ethanone compounds of Formula IV can be obtained by the reaction of an acetyl compound of Formula V with a fluoropyridine, fluoroquinoline, fluoropyrimidine, fluoropyridazine, or fluoropyrazine compound of Formula VI. Chloroheterocycles can often be used as well.

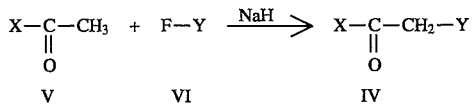

This method is especially valuable for the preparation of compounds of Formula IV wherein Y is an optionally substituted 2- or 4-pyridinyl, 2- or 4-pyrimidinyl, 2-pyrazinyl, 3- or 4-pyridazinyl, or 2-quinolinyl moiety. The reaction can be carried out by adding a solution of the acetyl compound V to a slurry of sodium hydride in an inert solvent, such as tetrahydrofuran or toluene, with agitation. The resultant mixture is maintained at about 0° C. to 120° C., the fluoroheterocycle or chloroheterocycle is added, and the mixture is allowed to react. The mixture is then cooled, quenched with an acid, and the desired product recovered by conventional means.

Other of the ethanone compounds of Formula IV can be obtained by the reaction of a carboxylic acid ester compound of Formula VII wherein X is defined as above with a methylpyridine, methylquinoline, methylpyridazine, methylpyrazine, or methylpyrimidine compound of Formula VIII wherein Y is as defined above.

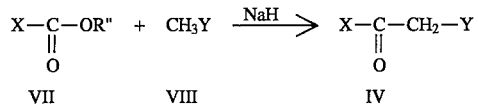

The reaction can be carried out by allowing the compound of Formula VIII to react with a slurry of sodium or potassium hydride in an inert solvent, such as tetrahydrofuran, adding the carboxylic acid ester of Formula VII, and allowing the mixture to react. The resultant reaction mixture is quenched with an acid, such as hydrochloric acid, or an acidic salt, such as ammonium chloride, and the desired product is recovered by conventional means.

Still other compounds of Formula IV can be prepared by hydration of a corresponding substituted acetylene compound of Formula IX wherein X and Y are as defined above.

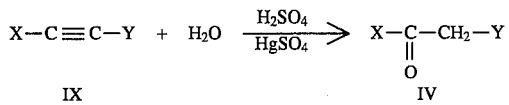

This method is especially valuable for preparing compounds of Formula IV wherein Y is an optionally substituted 3-pyridinyl, 3-quinolinyl, or 5-pyrimidinyl moiety. The reaction is generally carried out by heating at reflux for a few hours an aqueous mixture containing the compound of Formula IX, acetone, sulfuric acid, and mercuric sulfate and then recovering the ethanone compound by conventional means.

The acetylene compounds of Formula IX can be obtained by the reaction of a halopyridine, haloquinoline, halopyrimidine, halopyrazine, or halopyridazine compound of Formula X wherein Y is as defined above with an acetylene compound of Formula XI wherein X is as defined above.

Bromine is usually the preferred halogen (hal) moiety. The reaction can be carried out by heating for about an hour a mixture of the compounds of Formula X and XI in the presence of catalytic amounts of cuprous chloride and the bistriphenylphosphine complex with palladium dichloride in a solvent composed typically of a mixture of triethylamine and N,N-dimethylformamide. The desired product can be recovered by conventional means.

The compounds of Formulas IV, V, VII, and VIII are well known in the art or can be prepared by procedures well known in the art. For example, 5-trifluoromethyl-2-chloropyrazine can be made from 5-chloropyrazine-2-carboxylic acid by successive treatments with a mixture of phosphorus pentachloride and phenylphosphonic dichloride and a mixture of hydrogen fluoride and antimony trichloride using conditions that are well known for similar conversions of pyridinecarboxylic acids.

The substituted phenyl isocyanates and most of the heterocyclic isocyanates of Formula II are well known in the art and are readily available or can be prepared by known methods. Substituted pyridinyl, quinolinyl, pyrimidinyl, pyridazinyl, and pyrazinyl isocyanates can be prepared from the corresponding carboxylic acids by conversion to the corresponding azides and subsequent thermal rearrangement as is taught in the art. These isocyanates can, alternatively, be prepared from the corresponding optionally substituted aminopyridine, aminoquinoline, aminopyrimidine, aminopyridazine, or aminopyrazine compound by conversion to the corresponding optionally substituted N-pyridinyl-, N-quinolinyl-, N-pyrimidinyl-, N-pyridazinyl-, or N-pyrazinylcarbamate compound. This is typically accomplished by allowing the aminoheterocycle to react with phenyl chloroformate in the presence of an acid acceptor. The phenyl N-heterocyclylcarbamates readily dissociate into the desired heterocyclyl isocyanates on thermolysis as is taught in the art. It is often convenient to prepare these isocyanates in situ in the carbamoylation reaction because some of them lack storage stability. When this alternative procedure is followed, the appropriate phenyl N-heterocyclylcarbamate compound is substituted for the isocyanate compound in the procedure described hereinabove and, typically, an amine catalyst, such as 1,8-diazabicyclo[5,4,0]undec-7-ene, is added.

The insecticidal compounds of the present invention can be used directly to kill insects, but it is generally preferable to first prepare an insecticidal composition containing one or more of the compounds in combination with an agriculturally acceptable adjuvant or carrier. Suitable adjuvants or carriers should not be phytotoxic to valuable crops, particularly at the concentrations employed in applying the compositions for insect control in the presence of crops, and should not react chemically with the dihydropyrazole compound active ingredients or other composition ingredients. Such mixtures can be designed for direct application or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the insecticidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic, or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorant, penetration aids, spreading agents, sticking agents, dispersing agents, thickening agents, freeze point depressants, antimicrobial agents, and the like. The compositions can also contain other compatible components, for example, other insecticides or fungicides, herbicides, and the like and can be formulated with solid, particulate fertilizer carriers such as ammonium nitrate, urea and the like or with liquid fertilizers.

The concentration of the active ingredients in the insecticidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to insects or their locus generally contain about 0.001 to about 5 weight percent active ingredient and preferably contain about 0.01 to about 1.0 percent. Granular formulations containing about 1 to about 25 percent active ingredient are often employed and applied without further dilution.

The present compositions can be applied by the use of conventional ground or aerial dusters and sprayers, and by other conventional means known to those skilled in the art.

The insecticidal 3,4,N-triaryl-4,5-dihydro-1H-pyrazole-1-carboxamide compounds of the present invention are useful for the kill and control of a wide variety of insects and can be employed to protect crops and livestock as well as the public health. Insects that live on foliage, in the soil, and in other environments can be controlled. Insects of the orders Lepidoptera, Coleoptera, and Orthoptera are generally controlled. Insects of the order Lepidoptera, especially those of the genera Heliothis and Spodoptera, are usually especially well controlled, as are those of the genus Blattella. Such insects include tobacco budworm, beet armyworm, and german cockroach. The control of insects infesting crops, such as corn, cotton, rice, wheat, soybeans, and vegetables, is a preferred use of these compounds. Control of insects is generally achieved when at least about 0.01 kg/Ha is applied to foliage or other surfaces or when at least about 0.1 kg/Ha is applied to soil.

EXPERIMENTAL

General

Reagents and solvents were used as purchased from commercial suppliers. All reactions involving organometallic reagents were conducted in a dry nitrogen atmosphere using oven-dried glassware. Thin layer chromatography (TLC) plates were visualized via ultraviolet (UV) light. Melting points (pyrex capillary) were uncorrected. All evaporations were performed under reduced pressure. Column chromatography was performed using the flash method. Proton nuclear magnetic resonance spectroscopy (1H NMR) was performed using a Varian XL200 or Brucker AM400 spectrometer in CDCl$_3$ as solvent, unless otherwise noted. 1H NMR data are presented as: chemical shift in parts per million (ppm) downfield from tetramethylsilane (multiplicity, number of hydrogens, coupling constant(s) in Hertz (Hz)). Carbon nuclear magnetic resonance (13C NMR) was performed using a Brucker AM400 spectrometer operating at 101 megahertz in CDCl$_3$ solvent, unless otherwise noted. 13C NMR data are presented as: chemical shift in ppm downfield from tetramethylsilane and where appropriate (multiplicity, C-F coupling constant in Hertz). Infrared (IR) spectroscopy was performed on a Nicolet 5DXC FT-IR spectrometer.

EXAMPLE 1

Preparation of 2-(Trifluoromethyl)-2-pyridinyl)-1-(4-chlorophenyl)ethanone.

4'-Chloroacetophenone (16 milliliters (mL), 19 grams (g), 120 millimoles (mmol)) was added rapidly dropwise to a stirring 21° C. slurry of sodium hydride (17.1 g, 428 mmol, freed of mineral oil by a hexane wash) in tetrahydrofuran (THF) (280 mL). After 1 hour (hr), the mixture was heated at reflux for 1 hr, then cooled to 21° C. 2-Fluoro-5-(trifluoromethyl)pyridine was added rapidly dropwise to the stirring slurry causing a rapid color change to dark red. The solution was heated at reflux for 17 hr, at which time gas chromatography (GC) analysis showed complete conversion. The mixture was cooled to 0° C. and quenched by careful sequential addition of acetic acid (12 mL, 13 g, 210 mmol), water (125 mL), acetic acid (12 mL, 13 g, 210 mmol), and water (125 mL). The layers were treated separately due to the propensity of this material to form serious emulsions. The aqueous layer was extracted with ether (2×100 mL). The combined organic layer was extracted with water and brine, dried over magnesium sulfate, decolorized with activated charcoal, filtered, and evaporated to a wet brown solid residue. 1H NMR showed a 59:41 molar ratio of ketone to enol ether. The residue was triturated with hexane and applied to a porous plate to obtain a pale yellow solid. The hexane solvent was evaporated and the residue combined with the solid. The mixture was purified by flash chromatography, eluting with methylene chloride, to obtain 12.6 g (50 percent of theory) of the title compound as a yellow solid melting at 114°–116° C. All attempts to recrystallize the compound resulted in decomposition.

Elemental Analysis:
Calcd. for C$_{14}$H$_9$ClF$_3$NO: C, 56.11; H, 3.03; N, 4.67 Found: C, 55.71; H, 3.01; N, 4.59.

The following were prepared similarly:

2-(6-Fluoro-2-pyridinyl)1-(4-fluorophenyl)ethanone; a semi-solid (63 percent yield);
Elemental Analysis:
Calcd. for C$_{13}$H$_9$F$_2$NO: C, 66.95; H, 3.89; N, 6.01 Found: C, 67.11; H, 4.02; N, 6.09.

2-(5-(Trifluoromethyl)-2-pyridinyl)-1-(4-fluorophenyl)ethanone; a yellow powder melting at 82°–83° C. and decomposing on recrystallization (45 percent of theory);
1H NMR (ketone tautomer) δ4.53 (s, 2), 7.13 (dd, 2, J=8.5, 8.5), 7.44 (d, 1, J=8.0), 7.85 (m, 1), 8.08 (dd, 2, J=5.4, 8.9), 8.81 (m, 1); 1H NMR (enol tautomer) δ6.06 (s, 1), 7.09 (dd, 2, J=8.7, 8.7), 7.13 (d, 1, J=8.5), 7.79 (dd, 1, J=2.4, 7.9), 7.83 (dd, 2, J=5.4, 9.0), 8.57 (br s, 1), 14.97 (s, 1).
Elemental Analysis:
Calcd. for C$_{14}$H$_9$F$_4$NO: C, 59.37; H, 3.20; N, 4.95 Found: C, 59.72; H, 3.07; N, 4.82.

2-(6-Chloro-2-quinolinyl)-1-(4-chlorophenyl)ethanone; an orange solid melting at 194°–195° C. (50 percent yield);
Elemental Analysis:
Calcd. for C$_{17}$H$_{11}$Cl$_2$NO: C, 64.58; H, 3.51; N, 4.43 Found: C, 64.58; H, 3.46; N, 4.41.

2-(7-Chloro-2-quinolinyl)-1-(4-chlorophenyl)ethanone; orange solid melting at 181°–182° C. (34 percent yield);
Elemental Analysis:
Calcd. for C$_{17}$H$_{11}$Cl$_2$NO: C, 64.58; H, 3.51; N, 4.43 Found: C, 64.74; H, 3.73; N, 4.65.

2-(3-Fluoro-5-(trifluoromethyl)-2-pyridinyl)-1-(4-fluorophenyl)ethanone; a yellow powder (88 percent yield).

2-(5-Cyano-2-pyridinyl)-1-(4-chlorophenyl)ethanone; tan needles melting at 169°–170° C. (80 percent yield);
Elemental Analysis:
Calcd. for C$_{14}$H$_9$ClN$_2$O: C, 65.51; H, 3.53; N, 10.91 Found: C, 64.92; H, 3.27; N, 10.66.

2-(6-Chloro-4-pyrimidinyl)-1-(4-fluorophenyl)ethanone; yellow crysals melting at 98° C. (26 percent yield);
Elemental Analysis:
Calcd. for C$_{12}$H$_8$ClFN$_2$O: C, 57.50; H, 3.22; N, 11.18 Found: C, 57.60; H, 2.96; N, 11.01.

2-(5-Chloro-2-pyridinyl)-1-(4-fluorophenyl)ethanone; yellow needles melting at 95°–96° C. (34 percent yield);
Elemental Analysis:
Calcd. for C$_{13}$H$_9$ClFNO: C, 62.54; H, 3.63; N, 5.61 Found: C, 62.72; H, 3.71; N, 5.63.

2-(5-Trifluoromethyl-2-pyrazinyl)-1(4-fluorophenyl)ethanone; yellow solid melting at 97°–100° C. (76 percent yield);
Elemental Analysis:
Calcd. for C$_{13}$H$_8$F$_4$N$_2$O: C, 54.94; H, 2.84; N, 9.86 Found: C, 55.24; H, 2.75; N, 10.08.

2-(6-Chloro-2-pyrazinyl)-1-(4-fluorophenyl)ethanone; ivory plates melting at 88.5°–90° C. (82 percent yield);
Elemental Analysis:
Calcd. for C$_{12}$H$_8$ClFN$_2$O: C, 57.50; H, 3.22; N, 11.18 Found: C, 57.78; H, 3.45; N, 11.34.

EXAMPLE 2

Preparation of 1-(4-Chlorophenyl)-2-(6-chloro-3-pyridazinyl)-1-ethanone.

Potassium hydride (6.86 g of 35 percent in mineral oil, 60 mmol, washed 3 times with hexane to remove the mineral oil) and 100 mg of 18-crown-6 ether catalyst were placed in a flask under argon and 80 mL of tetrahydrofuran (THF) was added. 3-Chloro-6-methylpyridazine (2.57 g, 22 mmol) as a solution in 7 mL of THF was added dropwise with stirring at ambient temperature over a 50 min period. The resulting slurry was cooled to −40° C. and a solution of methyl 4-chlorobenzoate (3.75 g, 22 mmol) in 5 mL of THF was added with stirring and cooling over a 5 min period. The mixture was allowed to warm to ambient temperature and was stirred for 8 hr at which time all of the 3-chloro-6-methylpyridazine had been consumed as determined by TLC. The mixture was poured into 200 mL of saturated aqueous ammonium chloride solution and the phases were separated. The aqueous phase was extracted 3 times with 100 mL portions of methylene chloride and all of the organic phases were combined and filtered through a plug (5 cm×15 cm) of silica gel. The silica gel was extracted with a 10:90 mixture of ether and methylene chloride until the eluent was nearly colorless and the eluent was combined with the filtrate and concentrated by evaporation under reduced pressure. The residue was triturated with hexane and the solids were recovered by filtration and dried to obtain the title compound in 41 percent yield as a gold colored solid. An analytical sample melting at 152.5°–153.5° C. was obtained by recrystallization from hexane/acetone.

Elemental Analysis:
Calcd. for $C_{12}H_8Cl_2N_2O$: C, 53.96; H, 3.02; N, 10.49 Found: C, 53.68; H, 3.03; N, 10.24.

EXAMPLE 3

Preparation 5-(4-(Fluorophenyl)ethynyl)pyrimidine.

A mixture of 5-bromopyrimidine (3.3 g, 22 mmol), p-fluorophenylacetylene (2.64 g, 22 mmol), cuprous iodide (80 mg, 0.44 mmol), and palladium dichloride bistriphenylphosphine complex (310 mg, 0.44 mmol) in 20 mL of a 50:50 mixture of triethylamine and N,N-dimethylformamide was prepared and heated at 100° C. with stirring for 3 hr. The volatiles were then removed by evaporation under reduced pressure. The residue was taken up in 30 mL of chloroform and the resulting solution extracted with 100 mL of water and 100 mL of brine, dried over magnesium sulfate, and concentrated by evaporation under reduced pressure to obtain 4.26 g (97 percent of theory) of the title compound as a solid melting at 98° C.

1H NMR $\delta 7.0$ (dd, 2), 7.5 (dd, 2), 8.8 (s, 1), 9.1 (s, 1);
Elemental Analysis:
Calcd. for $C_{12}H_7FN_2$: C, 72.72; H, 3.56; N, 14.13 Found: C, 72.96; H, 3.65; N, 13.87.

The following were prepared similarly:
3-(Phenylethynyl)-6-chloroquinoline; a yellow powder melting at 95°–97° C. (43 percent yield);
Elemental Analysis:
Calcd. for $C_{17}H_{10}ClN$: C, 77.42; H, 3.82; N, 5.31 Found: C, 77.18; H, 3.79; N, 5.04.

3-(Phenylethynyl)-7-chloroquinoline; a tan powder melting at 114°–117° C. (65 percent yield);
Elemental Analysis:
Calcd. for $C_{17}H_{10}ClN$: C, 77.42; H, 3.82; N, 5.31 Found: C, 77.53; H, 3.85; N, 5.02.

3-(Phenylethynyl)pyridine a white solid melting at 49° C. (43 percent yield)
Elemental Analysis:
Calcd. for $C_{13}H_9N$: C, 87.12; H, 5.06; N, 7.81 Found: C, 86.97; H, 5.07; N, 7.70.

4-(Phenylethynyl)-2,6-di(trifluoromethyl)pyridine; a white solid melting at 111° C. (51 percent yield);
Elemental Analysis:
Calcd. for $C_{15}H_7F_6N$: C, 57.16; H, 2.24; N, 4.44 Found: C, 57.01; H, 2.22; N, 4.23.

2-(4-Fluorophenylethynyl)-5-chloropyrimidine; a white solid melting at 233° C. (d) (40 percent yield);
Elemental Analysis:
Calcd. for $C_{13}H_9N$: C, 61.95; H, 2.60 N, 12.01 Found: C, 61.33; H, 2.82; N, 11.50.

EXAMPLE 4

Preparation of 1-(4-Fluorophenyl)-2-(5-pyrimidinyl)ethanone.

A solution of 5-(4-(fluorophenyl)ethynyl)pyrimidine (2.90 g, 15 mmol) and mercuric sulfate (4.3 g, 15 mmol) in 100 mL of 70 percent aqueous acetone containing 10.4 g of 98 percent sulfuric acid was prepared and heated at reflux with stirring for 6 hr. The volatiles were then removed by evaporation under reduced pressure and the residue was made basic with aqueous ammonia and was then extracted with ether (2×100 mL) and 100 mL of methylene chloride. The combined organic extracts were extracted with brine (2×100 mL), dried over magnesium sulfate, filtered, and concentrated under reduced pressure to obtain 2.4 g of the title compound in crude form. This was column chromatographed, eluting with a 50:50 mixture of hexane and ethyl acetate, to obtain 1.56 g (49 percent of theory) of the title compound as fine white needles melting at 86° C.

IR absorptions at 1699, 1597, 1561, 1507, 1409, 1335, 1216, and 832 $cm^{-1}$;
1H NMR $\delta 4.26$ (s, 2), 7.15 (dd, 2), 8.0 (dd, 2), 8.61 (s, 2), 9.11 (s, 1);
Elemental Analysis:
Calcd. for $C_{12}H_9FN_2O$: C, 66.66; H, 4.20; N, 12.96 Found: C, 66.72; H, 4.22; N, 12.65.

The following were prepared similarly:
1-Phenyl-2-(7-chloro-3-quinolinyl)ethanone; white crystals melting at 160°–161° C. (62 percent yield);
Elemental Analysis:
Calcd. for $C_{17}H_{12}ClNO$: C, 72.47; H, 4.29; N, 4.97 Found: C, 72.57; H, 4.17; N, 4.80.

1-Phenyl-2-(6-chloro-3-quinolinyl)ethanone; white crystals melting at 113°–114° C. (74 percent yield);
Elemental Analysis:
Calcd. for $C_{17}H_{12}ClNO$: C, 72.47; H, 4.29; N, 4.97 Found: C, 71.80; H, 4.27; N, 4.77.

1-(4-Fluorophenyl)-2-(5-chloro-2-pyrimidinyl)ethanone; a yellow solid melting at 154° C. (53 percent yield);
Elemental Analysis:
Calcd. for $C_{12}H_8ClFN_2O$: C, 57.50; H, 3.22; N, 11.18 Found: C, 57.99; H, 3.42; N, 10.93.

1-(4-Fluorophenyl)-2-(5-(trifluoromethyl)-2-pyrimidinyl)ethanone; a white solid melting at 97° C. (76 percent yield);
Elemental Analysis:
Calcd. for $C_{13}H_8F_4N_2O$: C, 54.94; H, 2.84; N, 9.86 Found: C, 55.09; H, 2.82; N, 9.87.

EXAMPLE 5

Preparation of 2-(5-Trifluoromethyl-2-pyridinyl)-1-(4-chlorophenyl)-2-propen-1-one.

Acetic anhydride (19 mL, 21 g, 200 mmol) was added slowly to a stirring slurry of 2-(5-trifluoromethyl-2-pyridinyl)-1-(4-chlorophenyl)ethanone (12.1 g, 40.0 mmol) in bisdimethylaminomethane (22 mL, 16 g, 160 mmol) at 0° C. causing immediate solution. TLC showed complete conversion after 5 min and the mixture was partitioned between ether and water by adding these solvents and separating the layers. The organic layer was extracted with brine, dried over sodium sulfate, filtered, and evaporated under reduced pressure to obtain 13 g (99 percent of theory) of the title compound as a red oil.

1H NMR $\delta 5.92$ (s, 1), 6.73 (s, 1), 7.43 (d, 2, J=8.6), 7.64 (d, 1, J=8.3), 7.85 (d, 2, J=8.6), 7.92 (dd, 1, J=2.4, 8.3), 8.83 (m, 1).

The following were prepared similarly:
2-(6-Fluoro-2-pyridinyl)-1-(4-fluorophenyl)-2-propen-1-one; a red oil (97 percent yield).

2-(5-Trifluoromethyl-2-pyridinyl)-1-(4-fluorophenyl)-2-propene-1-one; a red oil (99 percent yield);
1H NMR $\delta 5.90$ (s, 1), 6.73 (s, 1), 7.12 (dd, 2, J=8.6, 8.6), 7.63 (d, 1, J=8.3), 7.91 (dd, 1, J=2.3, 7.6), 7.94 (dd, 2, J=5.4, 8.9), 8.83 (m, 1).

2-(5-Pyrimidinyl)-1-(4-fluorophenyl)-2-propen-1-one; an oil;
1H NMR $\delta 5.9$ (s, 1), 6.3 (s, 1), 7.1 (dd, 2), 7.9 (dd, 2), 8.8 (s, 2), 9.2 (s, 1).

2-(6-Chloro-3-quinolinyl)-1-phenyl-2-propen-1-one; a tan powder melting at 86°–87° C. (65 percent yield);
Elemental Analysis:
Calcd. for $C_{18}H_{12}ClNO$: C, 73.60; H, 4.12; N, 4.77 Found: C, 73.32; H, 4.14; N, 4.75.

2-(6-Chloro-2-quinolinyl)-1-(4-chlorophenyl)-2-propen-1-one; a tan powder melting at 117°–118° C. (50 percent yield);
Elemental Analysis:
Calcd. for $C_{18}H_{11}Cl_2NO$: C, 65.87; H, 3.38; N, 4.27 Found: C, 65.35; H, 3.38; N, 4.17.

2-(7-Chloro-3-quinolinyl)-1-phenyl-2-propen-1-one; an off-white powder melting at 95°–96° C. (69 percent yield);
Elemental Analysis:
Calcd. for $C_{18}H_{12}ClNO$: C, 73.60; H, 4.12; N, 4.77 Found: C, 74.54; H, 4.28; N, 4.70.

EXAMPLE 6

Preparation of 3-(4-Chlorophenyl)-4,5-di-hydro-4-(5-trifluoromethyl-2-pyridinyl)-1H-pyrazole.

Hydrazine hydrate (7.8 mL, 8.0 g, 160 mmol) was added slowly dropwise to a stirring solution of 2-(5-trifluoromethyl-2-pyridinyl)-1-(4-chlorophenyl)-2-propen-1-one in N,N-dimethylformamide (DMF) (40 mL) at 21° C. TLC showed complete conversion after 1 hr and the mixture was added dropwise with vigorous stirring to ice water to obtain a fluffy pale precipitate and a dark red-brown precipitate. The precipitates were collected by filtration and washed with water to obtain 14 g of solids. 1H NMR showed the two solids to be identical and to contain the title compound in 28 percent of theory yield.

1H NMR $\delta$3.73 (dd, 1, J=4.1, 9.8), 4.04 (dd, 1, J=10.2, 10.2), 4.78 (dd, 1, J=4.1, 11.0), 7.2–8.0 (m, 6), 8.8 (br s, 1).

The following were prepared similarly:
4,5-Dihydro-3-(4-fluorophenyl)-4-(6-fluoro-2-pyridinyl)-1H-pyrazole; a white solid (DMF solvent, 56 percent yield);

4,5-Dihydro-3-(4-fluorophenyl)-4-(5-trifluoromethyl-2-pyridinyl)-1H-pyrazole; a white solid (DMF solvent, 28 percent yield);

4,5-Dihydro-3-(4-chlorophenyl)-4-(5-(trifluoromethyl)-2-pyridinyl)-1H-pyrazole; (DMF solvent);

4,5-Dihydro-3-(4-chlorophenyl)-4-(5-cyano-2-pyridinyl)-1H-pyrazole; (trifluoroacetic acid solvent 4,5-Dihydro-3-(4-fluorophenyl)-4-(3-fluoro-5-(trifluoromethyl)-2-pyridinyl)-1H-pyrazole; (2-methylpyrazine and 3-chloropyridine solvents);

4,5-Dihydro-3-phenyl-4-(3-pyridinyl)-1H-pyrazole; (DMF solvent);

4,5-Dihydro-3-phenyl-4-(2,6-di(trifluoromethyl)-4-pyridinyl)-1H-pyrazole; (trifluoroacetic acid solvent);

4,5-Dihydro-3-phenyl-4-(6-chloro-3-quinolinyl)-1H-pyrazole; (DMF solvent, 88 percent yield);

4,5-Dihydro-3-phenyl-4-(7-chloro-3-quinolinyl)-1H-pyrazole; (DMF solvent, 85 percent yield);

3-(4-Chlorophenyl)-4-(7-chloro-2-quinolinyl)-4,5-dihydro-1H-pyrazole; (trifluoroacetic acid solvent);

3-(4-Chlorophenyl)-4-(6-chloro-2-quinolinyl)-4,5dihydro-1H-pyrazole; (trifluoroacetic acid solvent);

4,5-Dihydro-3-(4-fluorophenyl)-4-(5-pyrimidinyl)-1H-pyrazole; white solid (DMF solvent, 12 percent yield);

4,5-Dihydro-3-phenyl-4-(5-pyrimidinyl)-1H-pyrazole; (DMF solvent);

4,5-Dihydro-3-(4-fluorophenyl)-4-(5-chloro-2-pyrimidinyl)-1H-pyrazole; (trifluoroacetic acid solvent);

4,5-Dihydro-3-(4-fluorophenyl)-4-(6-chloro-4-pyrimidinyl)-1H-pyrazole; (trifluoroacetic acid solvent);

4,5-Dihydro-3-(4-chlorophenyl)-4-(6-chloro-4-pyrimidinyl)-1H-pyrazole; (trifluoroacetic acid solvent);

4,5-Dihydro-3-(4-fluorophenyl)-4-(2-(trifluoromethyl)-5-pyrimidinyl)-1H-pyrazole; (trifluoroacetic acid solvent);

4,5-Dihydro-3-(4-fluorophenyl)-4-(5-trifluoromethyl-2-pyrazinyl)-1H-pyrazole; (trifluoroacetic acid solvent);

4-(6-Chloro-2-pyrazinyl)-4,5-dihydro-3-(4-fluorophenyl)-1H-pyrazole; (trifluoroacetic acid solvent); and 3-(4-Chlorophenyl)-4-(6-chloro-3-pyridazinyl)-4,5-dihydro-1H-pyrazole; (trifluoroacetic acid solvent).

EXAMPLE 7

Preparation of 5-Chloro-2-picolinoyl azide.

A solution of sodium nitrite (1.4 g, 20 mmol) in water (7 mL) was added to a stirring solution of 5-chloro-2-picolinoyl hydrazide (2.49 g, 14.5 mmol) in 1M HCl (18 mL) at 0° C. at a rate such that the reaction temperature did not exceed 5° C. The resulting solids were collected by filtration, extracted with cold water, and diluted with ether and brine. The layers were separated and the organic phase was dried over magnesium sulfate, filtered, and evaporated to obtain 2.1 g (82 of theory) of the title compound.

EXAMPLE 8

Preparation of Phenyl N-(5-Trifluoromethyl-2-pyridinyl)carbamate.

Phenyl chloroformate (1.92 g, 12.3 mmol) was added to a stirring solution of 2-amino-5-trifluoromethylpyridine (2.0 g, 12.3 mmol) in pyridine (20 mL) at a rate which maintained the temperature at 21° C. The mixture was stirred for an additional 0.5 hr and the resulting precipitate was collected by filtration, extracted with ether, then dried to obtain 2.33 g (67 percent of theory) of the title compound as white crystals melting at 203° C.

1H NMR $\delta$7.25 (m, 3), 7.45 (m, 2), 8.0 (d, 2), 8.2 (d, 1), 8.7 (s, 1), 11.25 (s, 1).

Elemental Analysis:
Calcd. for $C_{13}H_9F_3N_2O_2$: C, 55.33; H, 3.21; N, 9.93 Found: C, 55.55; H, 3.22; N, 9.80.

The following compounds were prepared very similarly:
Phenyl N-(2-Trifluoromethyl-5-pyrimidinyl)carbamate; recovered as a crude oil (38 percent yield);

1H NMR $\delta$7.2–7.3 (m, 5), 9.1 (s, 2), 11.1 (s, 1).

Phenyl N-(6-Chloro-3-pyridinyl)carbamate; white crystals melting at 196° C. (73 percent yield);

1H NMR $\delta$7.1–7.6 (m, 5), 8.0 (dd, 1), 8.3 (dd, 1), 8.8 (s, 1).

EXAMPLE 9

Preparation of 3-(4-Chlorophenyl)-4,5-dihydro-N-(4-(methylthio)phenyl)-4-(5-trifluoromethyl-2-pyridinyl)-1H-pyrazole-1-carboxamide (Compound A).

4-(Methylthio)phenyl isocyanate (2.8 g, 17 mmol) was added to a stirring slurry of 3.8 g (3.0 mmol) of the product of Example 6 in methylene chloride (25 mL) at 21° C. causing rapid formation of a pale precipitate. TLC showed complete conversion after 19 hr and the precipitate, which was the corresponding bisaryl urea, was removed by gravity filtration. The filtrate was diluted with saturated aqueous sodium bicarbonate and the layers separated. The organic layer was dried over sodium sulfate, filtered, and evaporated to obtain a red oil which solidified on standing. This was purified by column chromatography eluting with 100:0 to 90:10 methylene chloride/ethyl acetate solvent. The product was recrystallized by dissolving in ethyl acetate and then adding hexane to obtain 0.44 g (29 percent of theory; 9 percent from the ethanone) of the title compound as fine white needles melting at 225°–226° C.;

Molecular ion in mass spectrum: 490;

IR absorptions at 3400, 1673, 1583, 1525, 1328, 1145, 1133, and 835 cm$^{-1}$;

1H NMR δ2.45 (s, 3), 4.22 (dd, 1, J=5.3, 11.6), 4.47 (dd, 1, J=11.8, 11.8), 5.01 (dd, 1, J=5.3, 11.9), 7.25 (d, 2, J=8.7), 7.28 (d, 2, J=8.7), 7.32 (d, 1, J=8.2), 7.47 (d, 2, J=8.7), 7.58 (d, 2, J=8.7), 7.86 (dd, 1, J=2.0, 8.2), 8.03 (br s, 1), 8.80 (m, 1);

13C NMR δ16.98, 53.22, 53.25, 119.82, 120.19, 121.73, 125.83 (q, J=67), 126.02 (q, J=301), 128.12, 128.46, 128.65, 129.08, 132.24, 134.75 (q, J=3), 136.01, 136.19, 147.00 (q, J=4), 151.63, 152.34, 163.13.

Elemental Analysis:

Calcd. for $C_{23}H_{18}ClF_3N_4OS$: C, 56.27; H, 3.70; N, 11.41 Found: C, 56.82; H, 3.76; N, 11.64.

The following compounds were prepared similarly:

B. 3-(4-Chorophenyl)-4,5-dihydro-N-(4-trifluoromethylphenyl)-4-(5-trifluoromethyl-2-pyridinyl)-1H-pyrazole-1-carboxamide; fine white needles melting at 232°–233° C. (29 percent yield; 8 percent from ethanone);

Molecular ion in mass spectrum: 512;

IR absorptions at 3380, 1680, 1533, 1328, 1147, 1135, 1115, 1066, and 837 cm$^{-1}$;

1H NMR (DMSO-d6) δ4.07, (dd, 1, J=5.1, 11.3), 4.43 (dd, 1, J=11.6, 11.6), 5.39 (dd, 1, J=5.1, 11.8), 7.44 (d, 2, J=8.6), 7.66 (d, 2, J=8.7), 7.80 (d, 1, J=8.3), 7.84 (d, 2, J=8.6), 7.92 (d, 2, J=8.6), 8.22 (dd, 1, J=2.1, 8.3), 8.87 (br d, 1, J=1.4), 9.55 (br s, 1).

Elemental Analysis:

Calcd. for $C_{23}H_{15}ClF_6N_4O$: C, 53.87; H, 2.95; N, 10.92 Found: C, 53.98; H, 2.95; N, 10.77.

C. 3-(4-Chlorophenyl)-4,5-dihydro-N-(4-trifluoromethoxyphenyl)-4-(5-trifluoromethyl-2-pyridinyl)-1H-pyrazole-1-carboxamide; fine white needles melting at 235°–236° C. (10 percent yield; 3 percent from ethanone);

Molecular ion in mass spectrum: 528;

IR absorptions at 3393, 1673, 1537, 1513, 1329, 1266, 1240, 1230, 1202, 1147, 1137, and 836 cm$^{-1}$;

1H NMR δ4.23 (dd, 1, J=5.3, 11.6), 4.49 (dd, 1, J=11.8, 11.8), 5.03 (dd, 1, J=5.3, 11.9), 7.18 (br d, 2, J=8.7), 7.29 (d, 2, J=8.8), 7.33 (d, 1, J=8.1), 7.56 (d, 2, J=9.1), 7.59 (d, 2, J=8.7), 7.88 (dd, 1, J=2.2, 8.2), 8.09 (br s, 1), 8.81 (dd, 1, J=0.8, 2.2);

Elemental Analysis:

Calcd. for $C_{23}H_{15}ClF_6N_4O_2$: C, 52.24; H, 2.86; N, 10.59 Found: C, 52.49; H, 2.84; N, 10.62.

D. 3-(4-Chlorophenyl)-N-(4-chlorophenyl)-4,5-dihydro-4-(5-trifluoromethyl-2-pyridinyl)-1H-pyrazole-1-carboxamide; fine white needles melting at 217°–218° C. (27 percent yield; 8 percent from ethanone);

Molecular ion in mass spectrum: 478;

IR absorptions at 3400, 1676, 1591, 1533, 1495, 1416, 1331, 1148, 1136, and 1083, cm$^{-1}$;

13C NMR δ53.21, 53.26, 120.33, 121.74, 121.82, 125.89 (q, J=33), 128.15, 128.23, 128.58, 129.00, 129.12, 134.78 (q, J=3), 136.31, 136.82, 147.06 (q, J=3), 151.51, 152.57, 163.05;

1H NMR δ4.22 (dd, 1, J=5.3, 11.6), 4.48 (dd, 1, J=11.8, 11.8), 5.02 (dd, 1, J=5.3, 11.9), 7.27 (d, 2, J=8.8), 7.29 (d, 2, J=8.7), 7.32 (d, 1, J=8.2), 7.49 (d, 2, J=8.9), 7.58 (d, 2, J=8.7), 7.87 (dd, 1, J=2.0, 8.2), 8.06 (br s, 1), 8.78 (d, 1, J=1.6);

Elemental Analysis:

Calcd. for $C_{22}H_{15}Cl_2F_3N_4O$: C, 55.13; H, 3.15; N, 11.69 Found: C, 55.02; H, 3.12; N, 11.76.

E. 4,5-Dihydro-3-(4-fluorophenyl)-4-(6-fluoro-2-pyridinyl)-N-(4-trifluoromethoxyphenyl)-1H-pyrazole-1-carboxamide; fine white needles melting at 189°–190° C. (40 percent yield; 13 percent from ethanone);

Molecular ion in mass spectrum: 462;

IR absorptions at 3400, 1678, 1604, 1537, 1513, 1423, 1272, 1223, 1202, 1157, and 845 cm$^{-1}$;

Elemental Analysis:

Calcd. for $C_{22}H_{15}F_5N_4O_2$: C, 57.15; H, 3.27; N, 12.12 Found: C, 57.07; H, 3.12; N, 12.21.

F. N-(4-Chlorophenyl)-4,5-dihydro-3-(4-fluorophenyl)-4-(6-fluoro-2-pyridinyl)-1H-pyrazole-1-carboxamide; fine white needles melting at 192°–193° C. (48 percent yield; 22 percent from ethanone);

Molecular ion in mass spectrum: 412;

IR absorptions at 3400, 1677, 1604, 1591, 1529, 1509, 1408, and 804 cm$^{-1}$;

Elemental Analysis:

Calcd. for $C_{21}H_{15}ClF_2N_4O$: C, 61.10; H, 3.66; N, 13.57 Found: C, 61.22; H, 3.69; N, 13.67.

G. 4,5-Dihydro-3-(4-fluorophenyl)-N-(4-trifluoromethylphenyl)-4-(5-trifluoromethyl-2-pyridinyl)-1H-pyrazole-1-carboxamide; white needles melting at 211°–212° C. (27 percent yield from ethanone);

Molecular ion in mass spectrum: 496;

IR absorptions at 3400, 1685, 1533, 1511, 1329, 1161, 1132, 1117, 1066, and 841 cm$^{-1}$;

Elemental Analysis:

Calcd. for $C_{23}H_{15}F_7N_4O$: C, 55.65; H, 3.05; N, 11.29 Found: C, 55.61; H, 3.17; N, 11.30.

H. 4,5-Dihydro-3-(4-fluorophenyl)-N-(4-trifluoromethoxyphenyl)-4-(5-trifluoromethyl-2-pyridinyl)-1H-pyrazole-1-carboxamide; white needles melting at 217°–218° C. (48 percent yield; 18 percent from ethanone);

Molecular ion in mass spectrum: 512;

IR absorptions at 3390, 1676, 1536, 1513, 1330, 1268, 1238, 1230, 1160, and 841 cm$^{-1}$;

Elemental Analysis:

Calcd. for $C_{23}H_{15}F_7N_4O_2$: C, 53.92; H, 2.95; N, 10.93 Found: C, 53.65; H, 2.82; N, 10.47.

I. N-(4-Chlorophenyl)-4,5-dihydro-3-(4-fluorophenyl)-4-(5-trifluoromethyl-2-pyridinyl)-1H-pyrazole-1-carboxamide; white needles melting at 209°–211° C. (36 percent yield; 20 percent from ethanone);

Molecular ion in mass spectrum: 462;

IR absorptions at 3390, 1677, 1533, 1510, 1330, 1236, 1160, 1133, and 841 cm$^{-1}$;

1H NMR δ4.22 (dd, 1, J=5.2, 11.6), 4.47 (dd, 1, J=11.7, 11.7), 5.02 (dd, 1, J=5.2, 11.8), 7.01 (dd, 2, J=8.6, 8.6), 7.27 (d, 2, J=8.8), 7.33 (d, 1, J=8.1), 7.49 (d, 2, J=8.8), 7.65 (dd, 2, J=5.3, 8.9), 7.87 (dd, 1, J=2.3, 8.2), 8.06 (br s, 1), 8.80 (m, 1);

Elemental Analysis:

Calcd. for $C_{22}H_{15}ClF_4N_4O$: C, 57.09; H, 3.27; N, 12.11 Found: C, 57.12; H, 3.16; N, 11.56.

J. 4,5-Dihydro-3-phenyl-4-(5-pyrimidinyl),N-(4-trifluoromethoxyphenyl)-1H-pyrazole-1-carboxamide; fine white crystals melting at 151° C. (12 percent yield over last two steps; 8 percent from ethanone);

1H NMR δ4.1 (dd, 1), 4.5 (dd, 1), 4.8 (dd, 1), 7.1 (m, 8), 8.1 (s, 1), 8.6 (s, 2), 9.1 (s, 1);

Elemental Analysis:

Calcd. for $C_{21}H_{15}F_3N_5O_2$: C, 59.02; H, 3.77; N, 16.39 Found: C, 58.86; H, 3.63; N, 16.31.

K. 4-(6-Chloro-3-quinolinyl)-4,5-dihydro-3-phenyl-N-(4-trifluoromethoxyphenyl)-1H-pyrazole-1-carboxamide; white solid melting at 203°–205° C. (57 percent yield; 48 percent from propenone);

Elemental Analysis:

Calcd. for $C_{26}H_{18}ClF_3N_4O_2$: C, 61.12; H, 3.55; N, 10.97 Found: C, 61.10; H, 3.42; N, 10.90.

L. 4,5-Dihydro-3-(4-fluorophenyl)-4-(5-trifluoromethyl-2-pyridinyl)-N-((4-trifluoromethylthio)phenyl)-1H-pyrazol-1-carboxamide; white needles melting at 224°–225° C. (11 percent yield from ethanone);
Elemental Analysis:
Calcd. for $C_{23}H_{15}F_7N_4OS$: C, 52.28; H, 2.86; N, 10.60
Found: C, 52.12; H, 2.67; N, 10.45.

M. 4,5-Dihydro-3-(4-fluorophenyl)-4-(4-fluoro-5-trifluoromethyl-2-pyridinyl)-N-(4-trifluoromethoxyphenyl)-1H-pyrazole-1-carboxamide; white needles melting at 213°–214° C. (13 percent yield from ethanone);
Elemental Analysis:
Calcd. for $C_{23}H_{14}F_8N_4O_2$: C, 52.09; H, 2.66; N, 10.56
Found: C, 52.11; H, 2.51; N, 10.42.

N. 3-(4-Chlorophenyl)-4-(5-cyano-2-pyridinyl)-4,5-dihydro-N-(4-hydro-N-(4-trifluoromethoxyphenyl)-1H-pyrazole-1-carboxamide; white needles melting at 185°–186° C. (21 percent yield from ethanone);
Elemental Analysis:
Calcd. for $C_{23}H_{15}ClF_3N_5O_2$: C, 56.86; H, 3.11; N, 14.41
Found: C, 56.57; H, 3.25; N, 14.48.

O. 3-(4-Chlorophenyl)-4-(6-chloro-2-quinolinyl)-4,5-dihydro-N-(4-trifluoromethoxyphenyl)-1H-pyrazole-1-carboxamide; white solid melting at 246°–249° C. (24 percent yield from propenone);
Elemental Analysis:
Calcd. for $C_{26}H_{17}Cl_2F_3N_4O_2$: C, 57.26; H, 3.14; N, 10.27
Found: C, 56.86; H, 2.98; N, 10.14.

P. 3-(4-Chlorophenyl)-4-(7-chloro-2-quinolinyl)-4,5-dihydro-N-(4-trifluoromethoxyphenyl)-1H-pyrazole-1-carboxamide; white solid melting at 203°–205° C. (31 percent yield from ethanone);
Elemental Analysis:
Calcd. for $C_{26}H_{17}Cl_2F_3N_4O_2$: C, 57.26; H, 3.14; N, 10.27
Found: C, 57.08; H, 3.24; N, 10.35.

Q. 4-(7-Chloro-3-quinolinyl)-4,5-dihydro-3-phenyl-N-(4-trifluoromethoxyphenyl)-1H-pyrazole-1-carboxamide; off-white solid melting at 187°–189° C. (15 percent yield from propenone);
Elemental Analysis:
Calcd. for $C_{26}H_{18}ClF_3N_4O_2$: C, 61.12; H, 3.55; N, 10.97
Found: C, 60.74; H, 3.60; N, 10.97.

R. 4,5-Dihydro-3-phenyl-4-(3-pyridinyl)-N-(4-trifluoromethoxyphenyl)-1H-pyrazole-1 -carboxamide; off-white solid melting at 187°–189° C. (15 percent yield from propenone);
Elemental Analysis:
Calcd. for $C_{22}H_{17}F_3N_4O_2$: C, 61.97; H, 4.02; N, 13.14
Found: C, 62.04; H, 3.99; N, 13.11.

S. 4,5-Dihydro-3-(4-fluorophenyl)-4-(5-pyrimidinyl)-N-(4-trifluoromethoxyphenyl)-1H-pyrazole-1-carboxamide; white solid melting at 147° C. (12 percent yield from ethanone);
Elemental Analysis:
Calcd. for $C_{21}H_{15}F_4N_5O_2$: C, 56.63; H, 3.39; N, 15.72
Found: C, 57.06; H, 3.32; N, 15.29.

T. 4-(5-Chloro-2-pyrimidinyl)-4,5-dihydro-3-(4-fluorophenyl)-N-(4-trifluoromethoxyphenyl)-1H-pyrazole-1-carboxamide; white solid melting at 174° C. (16 percent yield from ethanone);
Elemental Analysis:
Calcd. for $C_{21}H_{14}ClF_4N_5O_2$: C, 52.57; H, 2.94; N, 14.60
Found: C, 52.58; H, 2.90; N, 14.28.

U. 4,5-Dihydro-4-(2,6-di(trifluoromethyl)-4-pyridinyl)-3-phenyl-N-(4-trifluoromethoxyphenyl)-1H-pyrazole-1-carboxamide; white solid melting at 169° C. (5 percent yield from ethanone);
Elemental Analysis:
Calcd. for $C_{24}H_{15}F_9N_4O_2$: C, 51.25; H, 2.69; N, 9.96
Found: C, 51.25; H, 2.72; N, 9.72.

V. 4-(6-Chloro-4-pyrimidinyl)-4,5-dihydro-3-(4-fluorophenyl)-N-(4-trifluoromethoxyphenyl)-1H-pyrazole-1-carboxamide; white solid melting at 202° C. (12 percent yield from ethanone);
Elemental Analysis:
Calcd. for $C_{21}H_{14}ClF_4N_5O_2$: C, 52.57; H, 2.94; N, 14.60
Found: C, 52.17; H, 2.74; N, 14.50.

W. 4,5-Dihydro-3-(4-fluorophenyl)-N-(4-trifluoromethoxyphenyl)-4-(2-trifluoromethyl-5-pyrimidinyl)-1H-pyrazole-1-carboxamide; white solid melting at 174°–176° C. (25 percent yield from ethanone);
Elemental Analysis:
Calcd. for $C_{22}H_{14}F_7N_5O_2$: C, 51.47; H, 2.75; N, 13.64
Found: C, 51.64; H, 2.74; N, 13.63.

X. 4-(5-Chloro-2-pyridinyl)-4,5-dihydro-3-(4-fluorophenyl-N-(4-trifluoromethylphenyl)-1H-pyrazole-1-carboxamide; white needles melting at 186°–187° C. (17 percent yield from ethanone);
Elemental Analysis:
Calcd. for $C_{22}H_{15}ClF_4N_4O$: C, 57.09; H, 3.27; N, 12.11
Found: C, 56.69; H, 3.21; N, 11.85.

Y. 4,5-Dihydro-3-(4-fluorophenyl)-N-(4-trifluoromethylphenyl)-4-(5-trifluoromethyl-2-pyrazinyl)-1H-pyrazole-1-carboxamide; white solid melting at 232.5°–234° C. (23 percent yield from ethanone);
Elemental Analysis:
Calcd. for $C_{22}H_{14}F_7N_5O$: C, 53.13; H, 2.84; N, 14.08
Found: C, 53.48; H, 3.00; N, 13.94.

Z. 4-(6-Chloro-2-pyrazinyl)-4,5-dihydro-3-(4-fluorophenyl)-N-(4-trifluoromethylphenyl)-1H-pyrazole-1-carboxamide; creme solid melting at 227°–229° C. (45 percent yield from ethanone);
Elemental Analysis:
Calcd. for $C_{21}H_{14}ClF_4N_5O$: C, 54.38; H, 3.04; N, 15.10
Found: C, 54.50; H, 2.94; N, 14.90.

AA. 4-(6-Chloro-3-pyridazinyl)-3-(4-chlorophenyl)-4,5-dihydro-N-(4-trifluoromethylphenyl)-1H-pyrazole-1-carboxamide; off-white solid melting at 220°–222° C. (46 percent yield from ethanone);
Elemental Analysis:
Calcd. for $C_{21}H_{14}Cl_2F_3N_5O$: C, 52.52; H, 2.94; N, 14.58
Found: C, 52.85; H, 3.04; N, 14.36.

The following specific compounds can be made by the same general method: N-(4-cyanophenyl)-4,5-dihydro-3-(4-fluorophenyl-4-(5-trifluoromethyl-2-pyridinyl)-1H-pyrazole-1-carboxamide, N-(4-chloro-2-fluorophenyl)-4,5-dihydro-3-(4-fluorophenyl-4-(5-trifluoromethyl-2-pyridinyl)-1H-pyrazole-1-carboxamide, N-(6-chloro-3-pyridinyl)-4,5-dihydro-3-(4-fluorophenyl-4-(5-trifluoromethyl-2-pyridinyl)-1H-pyrazole-1-carboxamide, 4,5-dihydro-3-(4-pyridinyl)-N-(4-trifluoromethylphenyl)-4-(5-trifluoromethyl-2-pyridinyl)-1H-pyrazole-1-carboxamide, 3-(4-chlorophenyl)-4,5-dihydro-4-(6-methoxy-2-pyridinyl)-N-(4-trifluoromethylphenyl)-1H-pyrazole-1-carboxamide, 4,5-dihydro-3-(4-methoxyphenyl)-4-(4-pyridinyl)-N-(4-trifluoromethylphenyl)-1H-pyrazole-1-carboxamide, 4,5-dihydro-3-(4-fluorophenyl)-4-(5-trifluoromethyl-2-pyrimidinyl)-N-(4-trifluoromethylphenyl)-1H-pyrazole-1-carboxamide, 4,5-dihydro-3-(4-fluorophenyl)-4-(5-trifluoromethyl-2-pyrimidinyl)-N-(4-(trifluoromethoxy)phenyl)-1H-pyrazole-1-carboxamide, 4-(5-cyano-2-pyrimidinyl)-4,5-dihydro-3-(4-fluorophenyl)-N-(4-(trifluoromethoxy)phenyl)-1H-pyrazole-1-carboxamide, 4-(5-cyano-2-pyrimidinyl)-4,5-dihydro-3-(4-fluorophenyl)-N-(4-trifluoromethylphenyl)-1H-pyrazole-1-carboxamide, 4-(5-chloro-2-pyrimidinyl)-4,5-dihydro-3-(4-fluorophenyl)-N-(4-trifluoromethylphenyl)-1H-pyrazole-1-carboxamide, and 4-(5-cyano-2-pyridinyl)-4,5-dihydro-3-(4-fluorophenyl)-N-(4-trifluoromethylphenyl)-1H-pyrazole-1-carboxamide.

EXAMPLE 10

Effect on Tobacco Budworm and Beet Armyworm by Leaf Ingestion and/or Contact.

Stock solutions of the compounds to be tested having a known concentration were prepared by dissolving weighed amounts in a 90:10 mixture of high-purity acetone and ethanol and these solutions were diluted with distilled water (containing 0.05 percent by weight Tween 20™ surfactant) to obtain the spray solutions of known concentration employed. Greenhouse-grown cotton leaves of uniform age were cut into 2.5 cm diameter discs and one disc was placed in the bottom of each of a number of 30 mL plastic cups. The cups were then sprayed by means of a track sprayer applying 0.055 mL of spray solution per cup. The leaf discs were allowed to dry and then a single second-instar *H. virescens* (tobacco budworm) or *S. exigua* (beet armyworm) larva was added to each cup and each cup was capped with a perforated plastic lid. Ten cups were prepared for each insect species and each application rate and five applications rates were usually run. Treated cups were stored for 5 days at 25° C. and were then graded for mortality. Untreated controls and positive controls (cypermethrin) were run simultaneously. The amount of test chemical required to kill half of the larvae ($LD_{50}$) was calculated. Typical results are given in the following table.

| | INSECTICIDAL ACTIVITY ON LEPIDOTERA | | | |
|---|---|---|---|---|
| | BEET ARMYWORM | | TOBACCO BUDWORM | |
| Compound | Contact and Ingestion Test $LC_{50}$, ppm | Contact Test $LC_{50}$, ppm | Contact and Ingestion Test $LC_{50}$, ppm | Contact Test $LC_{50}$, ppm |
| A | 107 | — | >400 | — |
| B | 10.0 | >80 | 7.6 | >80 |
| C | 7.9 | — | 9.1 | — |
| D | 1.8 | 12.6 | 2.1 | 35.6 |
| E | 13.6 | — | 70.7 | — |
| F | >800 | — | 606 | — |
| G | 1.0 | 5.0 | 1.1 | 8.7 |
| H | 1.3 | <5.0 | 2.3 | 23.3 |
| I | 2.1 | <5.0 | 1.3 | 49.7 |
| J | >800 | — | 135 | — |
| K | 29.7 | — | 70.7 | — |
| L | 7.9 | >80 | 4.2 | 63.5 |
| M | 5.2 | 7.6 | 10.0 | 80 |
| N | 2.1 | 7.1 | 1.5 | 18.3 |
| O | >200 | — | >200 | — |
| P | 40.6 | — | 64.8 | — |
| Q | 13.4 | — | 30.8 | — |
| R | >400 | — | 186 | — |
| S | 490 | — | 50.0 | — |
| T | 1.4 | 2.2 | 1.3 | 7.5 |
| U | 37.9 | >100 | — | — |
| W | 7.5 | — | 6.1 | — |
| Y | >25 | 10.5 | — | — |
| Z | >100 | 75.8 | — | — |
| AA | 20.3 | 11.7 | — | — |

EXAMPLE 11

Effect on Tobacco Budworm and Beet Armyworm by Contact.

Stock solutions of the compounds to be tested having a known concentration were prepared by dissolving weighed amounts in a 90:10 mixture of high-purity acetone and ethanol and these solutions were diluted with distilled water (containing 0.05 percent by weight Tween 20™ surfactant) to obtain the spray solutions of known concentration employed. Teflon™ discs 5 cm in diameter were placed in plastic petri dishes of slightly larger diameter and these dishes were sprayed by means of a track sprayer applying 0.104 mL of spray solution per cup. The Teflon™ discs were allowed to dry, a single second-instar *H. virescens* (tobacco budworm) or *S. exigua* (beet armyworm) larva was placed on each Teflon™ disc, and each disc was capped with a plastic lid. Ten Teflon™ discs were prepared for each application rate and five application rates were usually run. Treated discs were stored for 24 hours at 25° C. and then the Teflon™ disc was removed and replaced with an untreated cotton leaf disc. After 5 more days of storage at 25° C. the dishes were graded for mortality. Untreated controls and positive controls (cypermethrin) were run simultaneously. The amount of test chemical required to kill half of the larvae ($LD_{50}$) was calculated. Typical results are given in the preceding table.

EXAMPLE 12

Effect on Cockroaches.

Two hundred ppm stock solutions of the compounds to be tested were prepared by dissolving 2.4 milligrams (mg) of each test compound in 12 mL of acetone; four lower concentration solutions were prepared by serial dilution using 3 mL of solution. A 0.5 mL portion of each test solution was pipetted onto 0.2 g of yellow corn meal placed in a small test tube cap (Fisher 02-706-33) and the mixture was placed in a fume hood overnight to allow the solvent to evaporate. This resulted in diets containing 500, 125, 31.2, 7.8, and 2.0 ppm of the test compounds to be used to determine activity by ingestion. Each cap was then placed in a 9 cm (centimeter) diameter Petri plate along with a 2 dram vial containing a cotton wick and water. A 0.5 mL portion of each test solution was also pipetted into a 20 mL borosilicate glass scintillation vial. The vials were placed on a roller mixer and the acetone was allowed to evaporate while the vials rolled. This resulted in vial walls containing 2.5, 0.63, 0.16, 0.04, and 0.01 micrograms/cm² to be used to determine activity by contact. Five late third or early fourth instar *Blattella germanica* nymphs weighing 0.01–0.04 g were placed in each vial and each Petri plate and covers were applied loosely to allow entry of air. Each Petri plate and vial was held at 27° C., the Petri plates for 21 days and the vials for 7 days. The percent of mortality was read periodically and at the end of the test.

Compounds G and T were tested and the 50 ppm solution was found to give 100 percent control after 7 days in the contact test and the 200 ppm solution was found to give 100 percent control and the 50 and 12.5 ppm solutions to give nearly 100 percent control after 21 days in the ingestion test.

What is claimed is:

1. A 1,2-diaryl-2-propen-1-one compound of the formula $$X-\underset{O}{\overset{\|}{C}}-\underset{CH_2}{\overset{\|}{C}}-Y$$

wherein

Y represents a 5-substituted-2-pyridinyl, 6-substituted-3-pyridinyl, (6 or 7)-substituted-2-quinolinyl, (6 or 7)-substituted-3-quinolinyl, 5-substituted-2-pyrimidinyl, 2-substituted-5-pyrimidinyl, 5-substituted-2-pyrazinyl, or 6-substituted-3-pyridazinyl moiety, each moiety being substituted in the designated position by one of F, Cl, Br, CN, COQ, $CF_3$, OR', SR', and OAr;

X represents Y, phenyl, or phenyl substituted in the 4-position with F, Cl, Br, CN, COQ, R, OR', SR', $NO_2$, or OAr and/or in the 3-position with F, Cl, Br, CN, R, or OR';

R represents $C_1$–$C_3$ alkyl, $C_2$–$C_3$ alkenyl, or $C_2$–$C_3$ alkynyl each optionally singly to completely substituted with fluorine or chlorine;

R' represents $C_1$–$C_3$ alkyl optionally singly to completely substituted with fluorine or chlorine;

R" represents $C_1$–$C_4$ alkyl, $C_3$–$C_4$ alkenyl, or $C_3$–$C_4$ alkynyl;

Ar represents phenyl optionally substituted with 1 or 2 compatible substituents selected from F, Cl, Br, CN, COQ, R, OR', SR', and $NO_2$; and Q represents OR", SR", $NH_2$, NHR, or $NR"_2$.

2. A compound according to claim 1 wherein X represents substituted phenyl.

3. A compound according to claim 2 wherein X represents phenyl substituted in the 4-position with F, Cl, Br, $CF_3$, and $OCF_3$, $OCF_2CF_2H$, or $SCF_3$.

4. A compound according to claim 1 wherein each Y moiety is substituted in the designated position by one of F, Cl, Br, CN, $CF_3$, and $OCF_3$.

5. A compound according to claim 4 wherein X represents phenyl substituted in the 4-position with F, Cl, Br, $CF_3$, $OCF_3$, $OCF_2CF_2H$, or $SCF_3$.

6. A compound according to claim 5: 1-(4-fluorophenyl)-2-(5-trifluoromethyl-2-pyridinyl)-2-propen-1-one.

7. A compound according to claim 5: 1-(4-chlorophenyl)-2-(5-cyano-2-pyridinyl)-2-propene-1-one.

8. A compound according to claim 5: 2-(5-chloro-2-pyrimidinyl)-1-(4-fluorophenyl)-2-propene-1-one.

9. A 1,2-diarylethanone compound of the formula

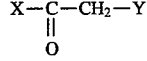

wherein

Y represents a 5-substituted-2-pyridinyl, 6-substituted-3-pyridinyl, (6 or 7)-substituted-2-quinolinyl, (6 or 7)-substituted-3-quinolinyl, 5-substituted-2-pyrimidinyl, 2-substituted-5-pyrimidinyl, 5-substituted-2-pyrazinyl, or 6-substituted-3-pyridazinyl moiety, each moiety being substituted in the desigented position by one of F, Cl, Br, CN, COQ, $CF_3$, OR', SR', and OAr;

X represents Y, phenyl, or phenyl substituted in the 4-position with F, Cl, Br, CN, COQ, R, OR', SR', $NO_2$, or OAr and/or in the 3-position with F, Cl, Br, CN, R, or OR';

R represents $C_1$–$C_3$ alkyl, $C_2$–$C_3$ alkenyl, or $C_2$–$C_3$ alkynyl each optionally singly to completely substituted with fluorine or chlorine;

R' represents $C_1$–$C_3$ alkyl optionally singly to completely substituted with fluorine or chlorine;

R" represents $C_1$–$C_4$ alkyl, $C_3$–$C_4$ alkenyl, or $C_3$–$C_4$ alkynyl;

Ar represents phenyl optionally substituted with 1 or 2 compatible substituents selected from F, Cl, Br, CN, COO, R, OR', SR', and $NO_2$; and Q represents OR", SR", $NH_2$, NHR, or $NR"_2$.

10. A compound according to claim 9 wherein X represents substituted phenyl.

11. A compound according to claim 10 wherein X represents phenyl substituted in the 4-position with F, Cl, Br, $CF_3$, and $OCF_3$, $OCF_2CF_2H$, or $SCF_3$.

12. A compound according to claim 9 wherein each Y moiety is substituted in the designated position by one of F, Cl, Br, CN, $CF_3$, and $OCF_3$.

13. A compound according to claim 12 wherein X represents phenyl substituted in the 4-position with F, Cl, Br, $CF_3$, $OCF_3$, $OCF_2CF_2H$, or $SCF_3$.

14. A compound according to claim 13: 1-(4-fluorophenyl)-2-(5-trifluoromethyl-2-pyridinyl)ethanone.

15. A compound according to claim 13: 1-(4-chlorophenyl)-2-(5-cyano-2-pyridinyl)ethanone.

16. A compound according to claim 13: 2-(5-chloro-2-pyrimidinyl)-1-(4-fluorophenyl)ethanone.

\* \* \* \* \*